(12) United States Patent
Michalak et al.

(10) Patent No.: US 7,582,772 B2
(45) Date of Patent: Sep. 1, 2009

(54) PROCESS FOR THE SYNTHESIS C-2, C-3 SUBSTITUTED N-ALKYLATED INDOLES USEFUL AS CPLA₂ INHIBITORS

(75) Inventors: Ronald S. Michalak, Congers, NY (US); Mahmut Levent, Bloomfield, NJ (US); Frederick J. Vyverberg, Chester, NY (US); Ara R. Boyajian, River Vale, NJ (US); Panolil Raveendranath, Monroe, NY (US); Michel Cantin, Saint-Laurent (CA); Alan Stockton, Longueuil (CA); Michael W. Winkley, Campbell Hall, NY (US); Mousumi Ghosh, Elmwood Park, NJ (US); Christoph Dehnhardt, New York, NY (US); Charles Guinosso, Chestnut Ridge, NY (US)

(73) Assignee: Wyeth, Madison, NJ (US)

( * ) Notice: Subject to any disclaimer, the term of this patent is extended or adjusted under 35 U.S.C. 154(b) by 500 days.

(21) Appl. No.: 11/207,072

(22) Filed: Aug. 18, 2005

(65) Prior Publication Data

US 2006/0041005 A1 Feb. 23, 2006

Related U.S. Application Data

(60) Provisional application No. 60/603,124, filed on Aug. 19, 2004.

(51) Int. Cl.
C07D 209/04 (2006.01)
C07C 255/58 (2006.01)
(52) U.S. Cl. .......................... 548/504; 564/99
(58) Field of Classification Search ................ 548/504; 564/99
See application file for complete search history.

(56) References Cited

U.S. PATENT DOCUMENTS

| | | | |
|---|---|---|---|
| 6,635,771 B2 | 10/2003 | McKew et al. | |
| 6,797,708 B2 | 9/2004 | McKew et al. | |
| 6,891,065 B2 * | 5/2005 | Wu et al. ........................ | 564/99 |
| 6,984,735 B2 | 1/2006 | McKew et al. | |
| 7,259,277 B2 | 8/2007 | Wu et al. | |
| 2003/0144282 A1 | 7/2003 | McKew et al. | |
| 2003/0149029 A1 | 8/2003 | McKew et al. | |
| 2003/0158405 A1 | 8/2003 | McKew et al. | |
| 2003/0166649 A1 | 9/2003 | McKew et al. | |
| 2004/0082785 A1 | 4/2004 | McKew et al. | |
| 2005/0020858 A1 | 1/2005 | Wu et al. | |
| 2005/0049296 A1 | 3/2005 | Dehnhardt et al. | |
| 2005/0070723 A1 | 3/2005 | Dehnhardt et al. | |
| 2005/0148770 A1 | 7/2005 | Michalak et al. | |
| 2005/0159613 A1 | 7/2005 | Wu et al. | |
| 2006/0014759 A1 | 1/2006 | McKew et al. | |

FOREIGN PATENT DOCUMENTS

WO WO03/048122 6/2003
WO WO2005/012235 2/2005

OTHER PUBLICATIONS

International Search report for PCT/US2005/029338.
Written Opinion of the International Searching Authority for PCT/2005/029338.
Appleton J. et al, "A mild and Selective C-3 reductive Alkylation of Indoles", Tetrahedron Letters. vol. 34, No. 9, 1993, 1529-1532.
Fagnola M. et al, "Solid-Phase synthesis of Indoles Using the Palladium-Catalysed Coupling of Alkynes with Iodoaniline Derivatives", Tetrahedron Letters, vol. 38, No. 13, 1997, 2307-2310.
Barluenga, J. et al. "Efficient reagents for the Synthesis of 5-, 7- and 5,7-Substitiuted Indoles Starting from Aromatic Amines: Scope and Limitations", J. Org. Chem., vol. 61, 1996, 5804-5812.
Sakamoto, T. et al, Condensed Heteroaromatic Ring Systems. XIII. One step Synthesis of 2-Substituted 1-Methylsulfonylindoles from N-(2-Halophenyl)methanesulfonamides, Chemical and Pharmaceutical Bullentin Pharmaceutical Society of Japan, vol. 36, No. 4, 1988, 1305-1308.
Shin K. et al, "An Expeditious Synthesis of 2,2'-Biindolyl", Synlett, 1995, 859-860.
Nilsson, B. et al, "Derivates of the Muscarinic Agent N-Methyl-N-(methyl-4-pyrrolidino-2-butynyl)acetamide", J. Med. Chem. (1988), vol. 31, pp. 577-582.

(Continued)

Primary Examiner—Kamal A Saeed
(74) Attorney, Agent, or Firm—Fish & Richardson P.C.

(57) ABSTRACT

The present invention provides method for making a compound of formula 1:

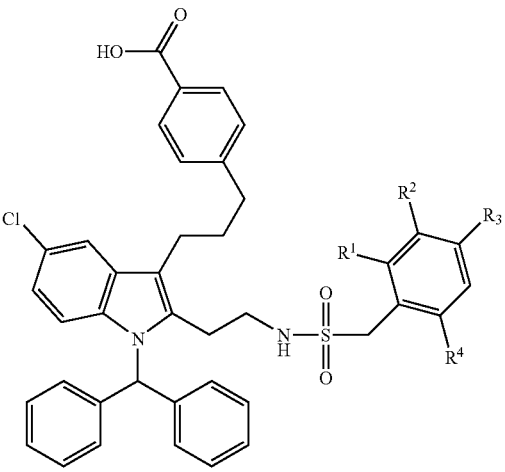

comprising the steps of reacting compounds of formulas 2 and 3:

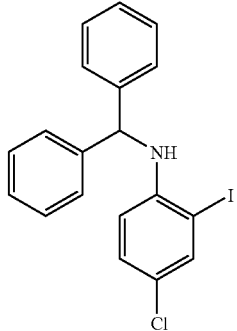

2

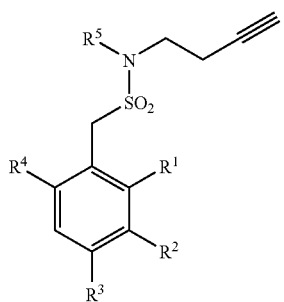

3 to produce a compound of formula 4:

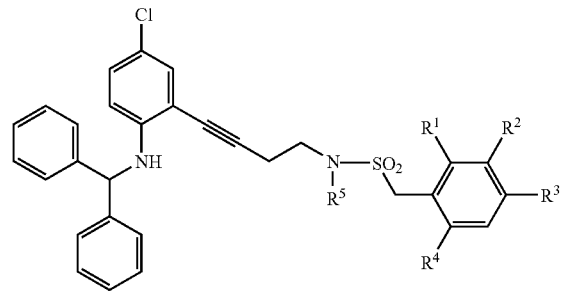

4 wherein $R^1$, $R^2$, $R^3$, $R^4$ and $R^5$ are defined as described herein. The compound of formula 4 is then converted to the compound of formula 1. The invention further comprises compounds of formulas 3 and 4 and methods for making compounds of formulas 3 and 4.

37 Claims, No Drawings

OTHER PUBLICATIONS

Fujiwara, J. et al, "Nucleaophilic Aromatic Substitution by Organoaluminum Reagents", J. Am. Chem. Soc., (1983) vol. 105, pp. 7177-7179.
Database Caplus Chemical Abstracts Service, Columbus, Ohio, US; database accession No. 1990-532816.
Deng, J. et al, "Synthesis and Characterization of Poly(N-propargylsulfamides)", Macromolecules, (2004), vol. 37, pp. 5538-5543.

* cited by examiner

PROCESS FOR THE SYNTHESIS C-2, C-3 SUBSTITUTED N-ALKYLATED INDOLES USEFUL AS CPLA$_2$ INHIBITORS

CROSS REFERENCE TO RELATED APPLICATIONS

This application claims priority benefit of U.S. Provisional Application Ser. No. 60/603,124 filed Aug. 19, 2004, which is incorporated by reference herein in its entirety.

FIELD OF THE INVENTION

This invention relates to a process for making substituted indoles useful as cPLA$_2$ inhibitors and intermediate compounds in that process.

BACKGROUND

Processes for alkylating the C-3 position of indoles are well known in the art. The effect of different metal cations, base concentration, and catalysts for the phase transfer alkylation of indoles under basic conditions has been studied. Alkylation of indoles can also proceed with catalytic amounts of acid. Trifluoroacetic acid and triethylsilane have been used in combination to simultaneously alkylate and reduce at the C-3 position of indoles. However, trifluoroacetic acid is incompatible with some acid sensitive functional groups, such as benzhydryl groups.

Known methods for producing N-alkylated indoles generally require expensive materials and processing. An efficient and economical method for producing N-alkylated indoles is therefore desirable.

SUMMARY OF THE INVENTION

The present invention provides method for making a compound of formula 1:

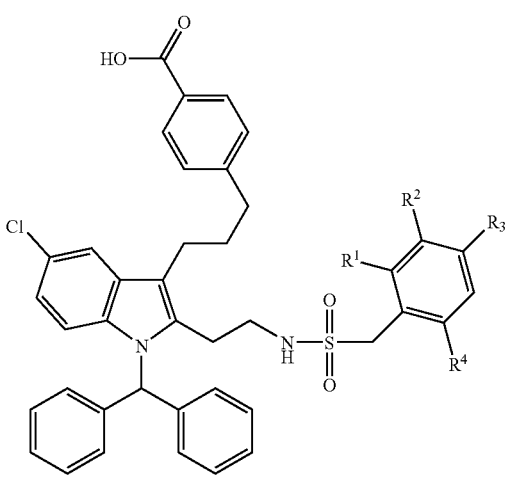

comprising the steps of reacting compounds of formulas 2 and 3:

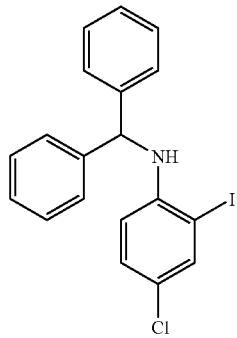

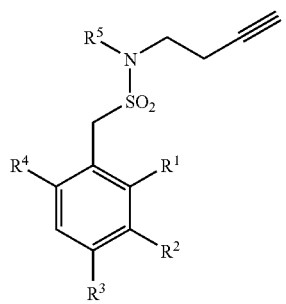

to produce an intermediate compound of formula 4:

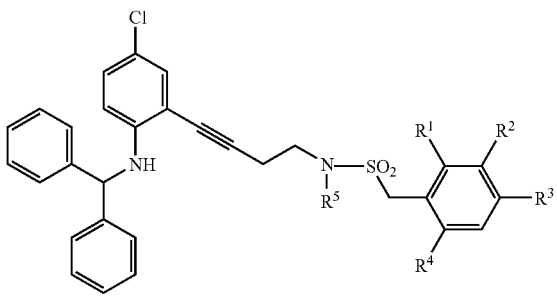

wherein R$^1$, R$^2$, R$^3$, R$^4$ and R$^5$ are defined as described herein. The reaction occurs in the presence of a base, a palladium catalyst, and a copper catalyst. The compound of formula 4 is then converted to the compound of formula 1.

The invention further comprises compounds of formulas 3 and 4 and methods for making compounds of formulas 3 and 4.

DETAILED DESCRIPTION OF THE PREFERRED EMBODIMENTS

The coupling reaction of a compound of formula 3, above, with N-substituted 2-iodo, 4-chloro anilines requires different reaction conditions depending on the identity of the aniline amino substituent. When the amino substituent is a trifluoroacetyl group, for example, the reaction is facile with relatively low levels of catalysts (e.g., about 1 mole % Pd catalyst and 2 mole % CuI) at moderate temperatures (e.g., less than 50° C.). However, when the amino substituent is a benzhydryl group, more Pd catalyst (e.g., about 5 mole % or more) is necessary, which increases the cost and complexity of the synthesis and purification.

It has been discovered that the coupling reaction of compounds of formulas 2 and 3 will proceed efficiently to produce the compound of formula 4 in high yield when the amount of palladium catalyst is reduced (e.g., about 0.5 mole % to about 1.5 mole %), provided that the copper catalyst is present in at least about 5 mole % and at least about 2 equivalents (i.e., about 200 mole %) of a base is used. The use of less palladium catalyst makes the method of the invention more efficient and economical.

The present invention provides method for making a compound of formula 1:

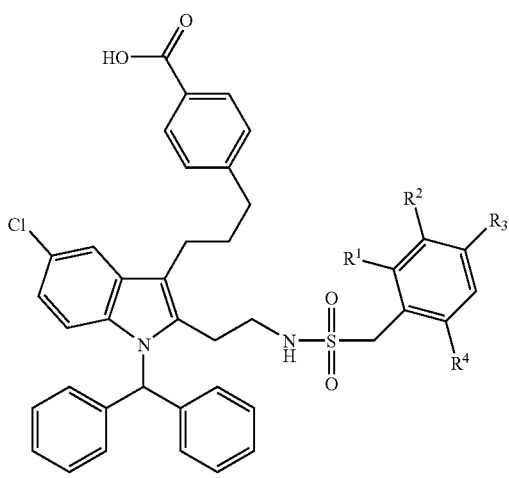

comprising the steps of reacting compounds of formulas 2 and 3:

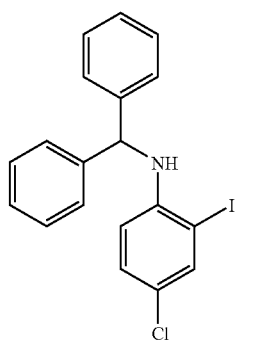

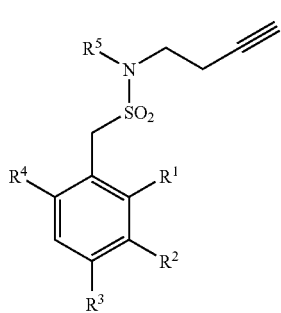

to produce an intermediate compound of formula 4:

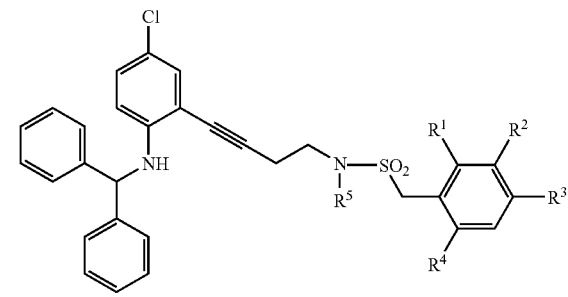

wherein $R^1$, $R^2$, $R^3$, and $R^4$ each is independently selected from the group consisting of H, halogen, —CN, —CHO, —$CF_3$, —$OCF_3$, —OH, —$NO_2$, —$C_{1-6}$ alkyl, —$C_{1-6}$ alkoxy, —$NH_2$, —NH($C_{1-6}$ alkyl), —N($C_{1-6}$ alkyl)$_2$, and —NHC(O)—$C_{1-6}$ alkyl, and $R^5$ is selected from the group consisting of H and —C(O)O—$C_{1-6}$ alkyl. The reaction occurs in the presence of a base, a palladium catalyst, and a copper catalyst. The compound of formula 4 is then converted to the compound of formula 1.

In some embodiments, $R^1$, $R^2$, $R^3$, and $R^4$ each is independently selected from the group consisting of H, halogen, —$CF_3$, and —$C_{1-6}$ alkyl. In certain embodiments, $R^1$ is H, $R^2$ is Cl, $R^3$ is Cl, and $R^4$ is H. In other embodiments, $R^1$ is —$CF_3$, $R^2$ is H, $R^3$ is H, and $R^4$ is H.

At least about 2 equivalents (e.g., about 2-4 equivalents, or about 3 equivalents) of base may be present in the reaction mixture. Suitable bases include, for example, trialkylamines (e.g., diisopropylethylamine or triethylamine), alkali metal carbonates (e.g., lithium carbonate, sodium carbonate, potassium carbonate, or cesium carbonate), alkali metal bicarbonates (e.g., lithium bicarbonate, sodium bicarbonate, potassium bicarbonate, or cesium bicarbonate), alkaline earth metal carbonates (e.g., magnesium carbonate, calcium carbonate, or barium carbonate), and alkaline earth metal bicarbonates (e.g., magnesium bicarbonate, calcium bicarbonate, or barium bicarbonate).

The palladium catalyst may be present in about 0.5 mole % to about 1.5 mole %. Any palladium catalyst useful in Sonogashira-type coupling reactions may be used, including, for example, $PdCl_2(PPh_3)_2$, $Pd(PPh_3)_4$, $Pd(CN)_2Cl_2$, $Pd(OAc)_2$, and $PdCl_2$ with appropriate phosphine ligands such as $PPh_3$, P(cyclohexyl)$_3$, or P(t-butyl)$_2$methyl.

The copper catalyst may be present in at least about 5:mole % (e.g., 5 mole % to about 15 mole %, or about 10 mole %). Any copper catalyst useful in Sonogashira-type coupling reactions may be used, including, for example, copper iodide (CuI).

Organic bases (e.g., trialkylamines) may be removed by distillation of the product mixture, typically under reduced pressure. An alcohol, such as isopropanol, may be added to keep minor impurities dissolved while the compound of formula 4 is precipitated by addition of an anti-solvent, such as water, which obviates the need to separate the product from water-soluble inorganic bases (e.g., alkalai and alkaline earth metal carbonates and bicarbonates). Using the process of this invention, compounds of formula 4 may be obtained in yields of at least about 90%, and at purities of at least about 95%.

The compound of formula 4 may be reacted with copper iodide to produce a compound of formula 5:

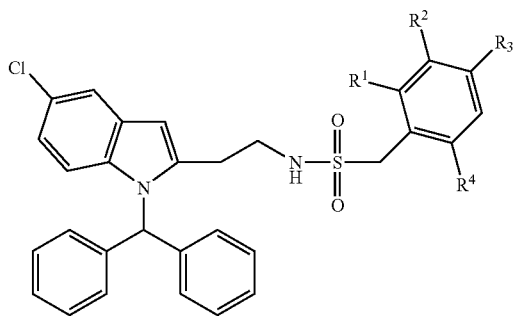

5

The compound of formula 5 may be reacted with a compound of formula 6:

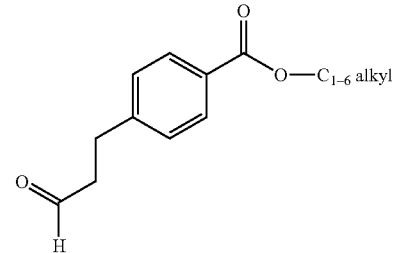

6 to produce a compound of formula 7:

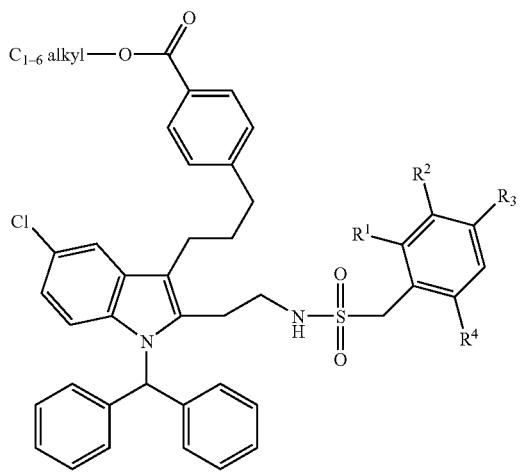

7

The compound of formula 7 may be reacted with a base to remove the ester $C_{1-6}$ alkyl group and produce the compound of formula 1. The compound of formula 7 may be isolated by crystallization prior to reacting with the base, or alternatively, the compound of formula 7 may be reacted with the base without prior purification.

The compound of formula 1 may be purified, for example, by recrystallization from an alcohol, such as ethanol.

The compound of formula 2 can be prepared by reacting 2-iodo-4-chloroaniline (obtained, for example, by iodination of p-chloroaniline, or by any other method known in the art) with benzhydrol in the presence of an acid such as an organic sulfonic acid (e.g., benzenesulfonic acid, p-toluenesulfonic acid, or the like), in an aprotic solvent (e.g., acetonitrile, toluene, or the like). In some embodiments this reaction proceeds slowly and requires slow addition of the benzhydrol to the 2-iodo-4-chloroaniline to achieve a good yield. Addition and reaction times can be reduced without reducing the yield or purity of the product by heating the reaction, for example, to at least about 75° C., or at least about 80° C., or to the reflux temperature of the solvent. The compound of formula 2 thus produced may be purified by precipitation and filtration, followed by trituration with a solvent (e.g., methanol) to remove impurities. The compound can be obtained in a purity of at least about 90% (e.g., about 98-99%) by this method.

The compound of formula 3 may be prepared by reacting a compound of formula 8 with a compound of formula 9:

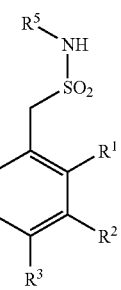

8

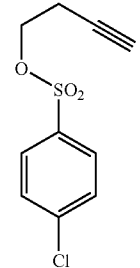

9 in the presence of a base, wherein $R^5$ is —C(O)O—$C_{1-6}$ alkyl (such as, for example, tert-butoxycarbonyl).

The invention also provides a method for making a compound of formula 4:

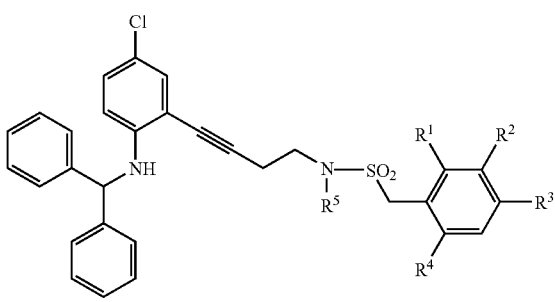

4 according to the methods described above. The invention further provides compounds of formula 4.

The invention further provides compounds of formula 3:

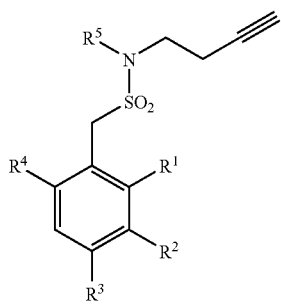

wherein $R^1$, $R^2$, $R^3$, and $R^4$ each is independently selected from the group consisting of H, halogen, —CN, —CHO, —$CF_3$, —$OCF_3$, —OH, —$NO_2$, —$C_{1-6}$ alkyl, —$C_{1-6}$alkoxy, —$NH_2$, —NH($C_{1-6}$ alkyl), —N($C_{1-6}$ alkyl)$_2$, and —NHC(O)—$C_{1-6}$ alkyl, and $R^5$ is selected from the group consisting of H and —C(O)O—$C_{1-6}$ alkyl. In some embodiments, $R^1$, $R^2$, $R^3$, and $R^4$ each is independently selected from the group consisting of H, halogen, —$CF_3$, and —$C_{1-6}$ alkyl. In certain embodiments, $R^1$ is H, $R^2$ is Cl, $R^3$ is Cl, and $R^4$ is H. In other embodiments, $R^1$ is —$CF_3$, $R^2$ is H, $R^3$ is H, and $R^4$ is H. In still other embodiments, $R^1$ is $CH_3$, $R^2$ is H, $R^3$ is H, and $R^4$ is $CH_3$. Examples of compounds of formula 3 include N-but-3-ynyl-C-(2,6-dimethylphenyl)methanesulfonamide, N-but-3-ynyl-C-(3,4-dichlorophenyl)methanesulfonamide, and N-but-3-ynyl-C-(2-[trifluoromethyl]phenyl) methane-sulfonamide.

The term mole % as used herein refers to the ratio of the moles of a reactant to the moles of the compound of formula 2 or of formula 3, whichever is less.

As used herein, the term halogen refers to fluorine, chlorine, bromine and iodine. The term alkyl includes both straight and branched chain alkyl groups. The term alkoxy refers to —O—alkyl, where alkyl is defined as described above.

An embodiment of the present invention is shown below in Scheme 1.

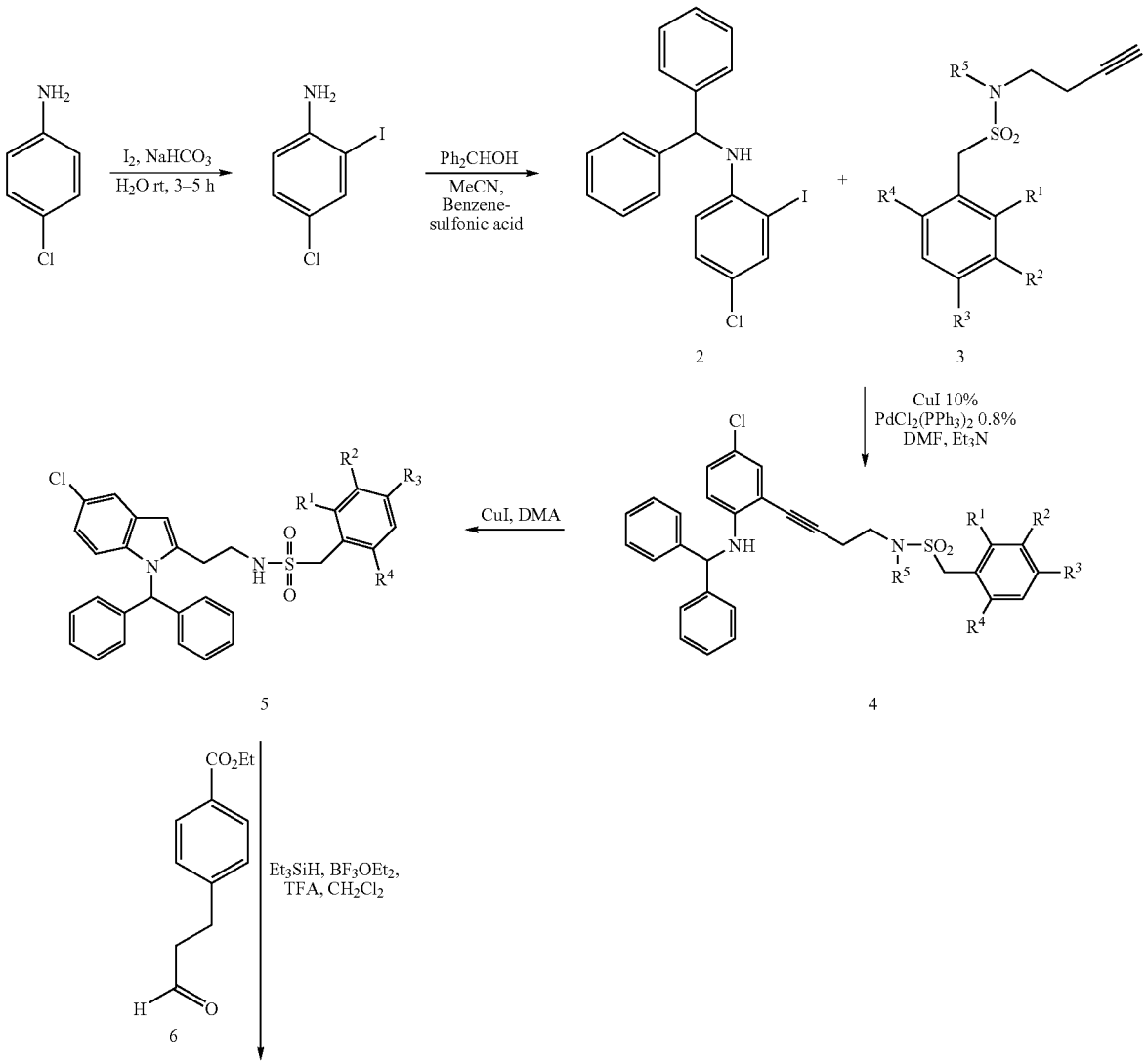

-continued

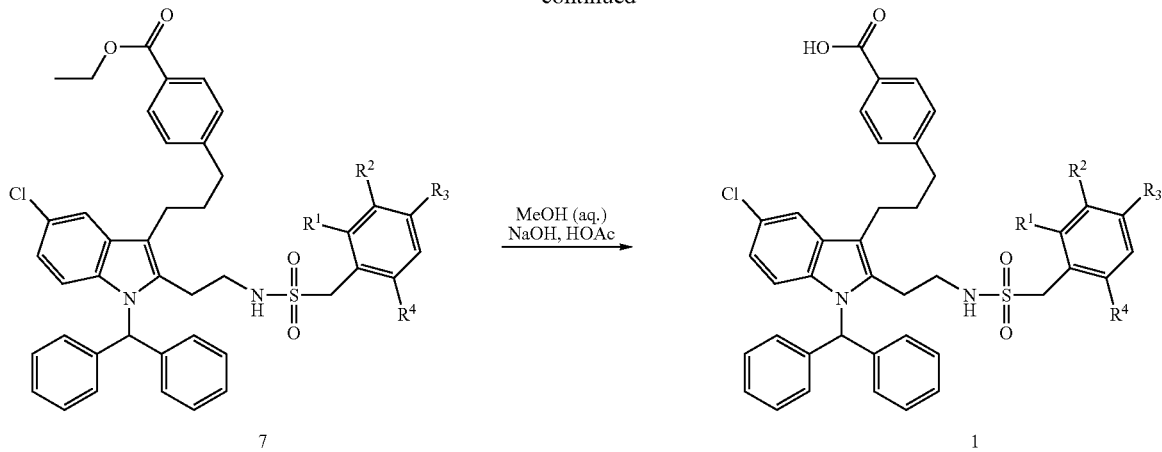

7 → 1

MeOH (aq.)
NaOH, HOAc

In the reaction between the compounds of formulas 2 and 3, about half of the palladium catalyst can be combined with the compound of formula 3 in a first mixture, and the other half can be combined with the compound of formula 2, the CuI, and the base in a second mixture. The first mixture can then be added slowly to the second.

The compound of formula 4 may be precipitated and recovered as a solid by filtration, leaving the bulk of the palladium catalyst in the mother liquor solution. If the palladium-catalyzed coupling reaction and indole cyclization reaction are concatenated, the palladium catalyst may be removed during an extractive workup, for example, by washing the organic product layer with an aqueous solution of N-acetylcysteine, a procedure known in the art. The solid precipitate may also be washed if additional palladium extraction is needed.

Following extraction of the palladium catalyst, the compound of formula 4 is reacted with copper iodide in an aprotic solvent to induce indole cyclization. If the $R_5$ group is a carbamate (e.g., tert-butoxycarbonyl), it will be removed during this step. When this reaction is run at higher temperatures, the rate of cyclization generally is more rapid and fewer impurities are found in the product. Suitable solvents include DMF, DMA, or the like. The reaction generally is run at a temperature at least about 100° C., preferably about 145-155° C. Although the reactants may be mixed all at once, it is preferable to slowly add the compound of formula 4 to a hot solution of the copper iodide, especially when the reaction is carried out on large scale.

The compound of formula 6 may be obtained by any method known in the art, for example, by reacting the corresponding alkyl 4-iodobenzoate with allyl alcohol in a stirred suspension of sodium bicarbonate, tetrabutyl-ammounium bromide and palladium (II) acetate in DMF. The compound of formula 6 may be purified, for example, by forming the metabisulfite salt 6a, as shown in Scheme 2 below.

Scheme 2

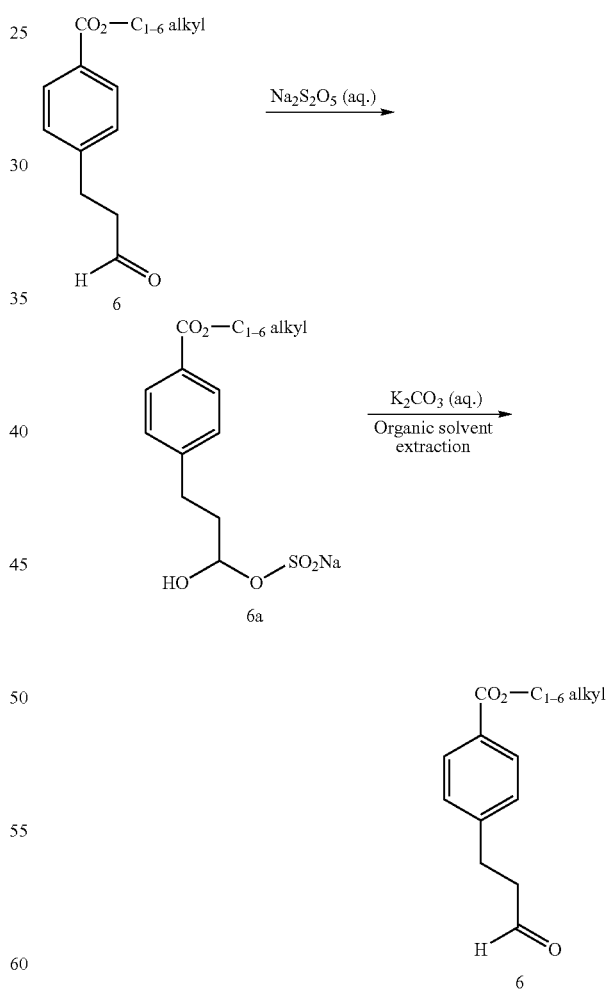

For example, the compound of formula 6 may be dissolved in a suitable organic solvent (e.g., toluene) and converted to the metabisulfite salt 6a by addition of an aqueous metabisulfite solution. Although Scheme 2 includes sodium metabisulfite (Na₂S₂O₅) as a reactant, other metabisulfite salts (e.g., potassium metabisulfite, calcium metabisulfite) may be used. Separation of the organic layer removes organic impurities. The metabisulfite salt 6a, which remains dissolved in the aqueous layer, can then be converted back to the compound of formula 6 by reacting it with a base (e.g., potassium carbonate) in a water-ethyl acetate mixture and separating the ethyl acetate layer to isolate the compound. Using this method, the compound of formula 6 can be isolated having a purity of greater than about 95%.

In one embodiment of the invention, the compounds of formulas 5 and 6 are reacted with boron trifluoride etherate, trifluoroacetic acid and triethylsilane in methylene chloride to produce the compound of formula 7.

The compound of formula 7 can be converted to the compound of formula 1 by treatment with base (e.g., a mixture of aqueous NaOH and THF in ethanol) followed by lowering the pH (using, for example, an acid such as aqueous acetic acid) to produce the compound of formula 1. The product may be precipitated, for example, by reducing the solvent volume and reducing the temperature.

Preferably, the compound of formula 7 is converted to the compound of formula 1 without previously isolating the compound of formula 7. Alternatively, the compound of formula 7 may be crystallized prior to conversion, for example, by evaporating the solvent to produce a syrup, and then stirring the syrup with ether and seed crystals. The compound may also be crystallized from an alcohol (e.g., methanol, ethanol, isopropanol, and the like) or any other suitable solvent.

The compound of formula 1 may be purified by recrystallization from a variety of solvent systems, for example, from toluene, toluene/heptane mixtures, ethyl acetate/heptane mixtures, and the like. Recrystallization from 100% ethanol has been shown to effectively purify the compound without reducing yield.

Scheme 3 illustrates a route for making a compound of formula 3.

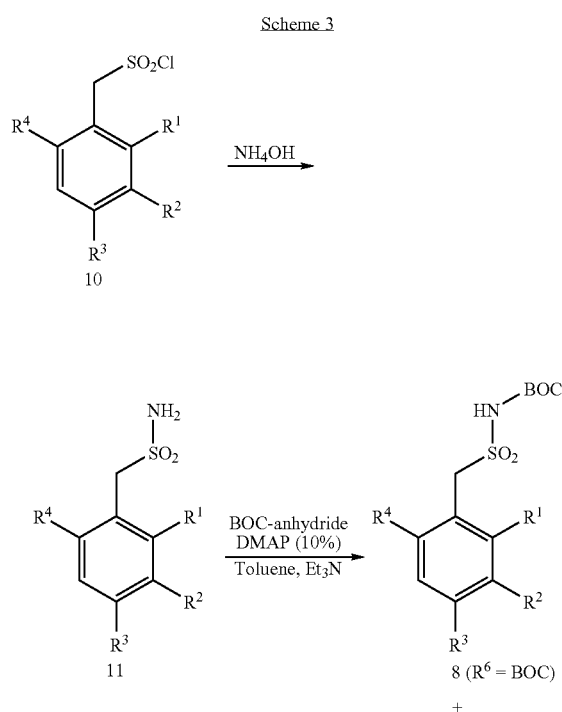

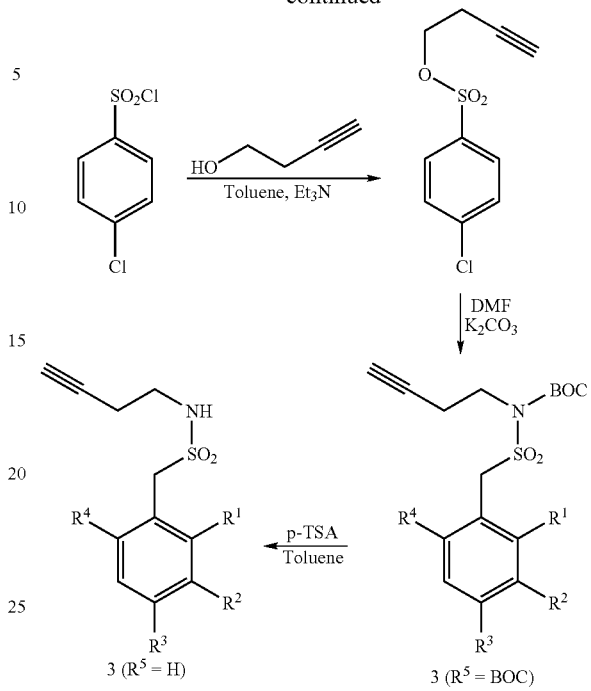

As illustrated in Scheme 3, the compound of formula 8 may be prepared, for example, by reacting a sulfonyl chloride 10 with aqueous or gaseous ammonia to form a sulfonamide 11, which can then be protected as a carbamate, for example, by reacting with tert-butoxycarbonyl anhydride (BOC-anhydride). The reaction may be run at elevated temperature (e.g., about 45° C.) in a solvent such as toluene and in the presence of 4-dimethylaminopyridune (DMAP) and triethylamine (Et₃N).

The compound of formula 9 may be prepared by reacting 3-butyn-1-ol with 4-chlorobenzenesulfonyl chloride in the presence of triethylamine in toluene. In this reaction, it is convenient to keep the reaction temperature below about 20° C., as the triethylamine hydrochloride salt byproduct precipitates and is readily separated by filtration. The product can be precipitated from the solution, for example, by reducing the solvent volume and adding propanol and cold water.

In one example according to the invention, the reaction between the compounds of formulas 8 and 9 occurs in the presence of potassium carbonate granules or powder in DMF at elevated temperatures (e.g., 50-55° C.). The last step of Scheme 2, the removal of the tert-butoxycarbonyl (BOC) group, is optional, since either compound can be used in the reaction in Scheme 1.

The reaction of compounds of formulas 8 and 9 is an example of a homopropargylation reaction. Homopropargylation generally involves an $SN_2$ reaction using a homopropargyl precursor containing a leaving group, such as a halogen or tosylate. The methods known in the art may not be suitable for weaker nucleophiles, however, especially if the compound includes base sensitive functional groups. The triflate group ($CF_3SO_3$—) has been shown to be a good leaving group, but is relatively expensive. A milder method known in the art for introducing the homopropargyl group involves a Mitsunobu type reaction with 3-butyn-1-ol and triphenylphosphine. This reaction, however, suffers from poor atom-economy.

Using the methods of the present invention, $SN_2$-type homopropargylation reactions can be achieved under relatively mild conditions by using the leaving group p-chlorophenylsulfonyl. The homopropargylation reaction is shown in Scheme 4 below, in which Nu represents a nucleophile.

Scheme 4

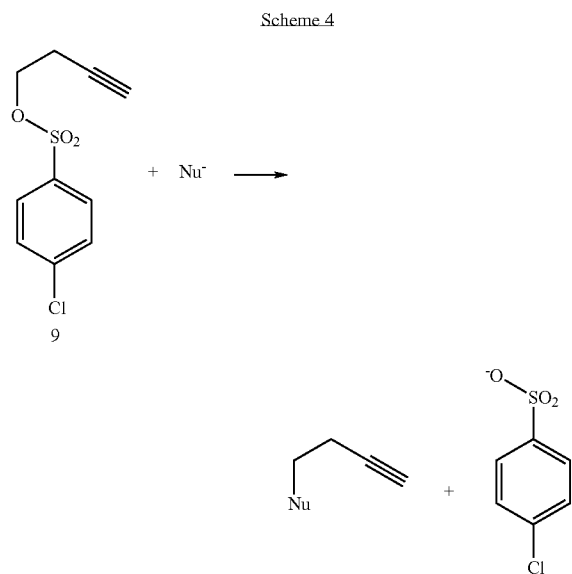

In addition to the advantages of relatively low cost and mild conditions, this process also has the advantage that the compound of formula 9 is a solid that can be prepared in high yield and is stable to extended storage at room temperature. The selectivity of homopropargylation using the compound of formula 9 is illustrated by the high yield (~90%) of the homopropargylations in the examples described herein, using only a slight (<10%) molar excess of the compound of formula 9.

Examples of compounds that can be synthesized using the methods of this invention include those in which the groups $R_{1-4}$ have one of the combinations of shown in the following table:

| Compound | $R^1$ | $R^2$ | $R^3$ | $R^4$ |
|---|---|---|---|---|
| A | $CH_3$ | H | H | H |
| B | $CH_3$ | H | H | $CH_3$ |
| C | $CF_3$ | H | H | H |
| D | H | $CF_3$ | H | H |
| E | H | H | $CF_3$ | H |
| F | $CF_3$ | H | H | $CF_3$ |
| G | H | H | Cl | H |
| H | Cl | H | H | H |
| I | Cl | H | Cl | H |
| J | H | Cl | Cl | H |
| K | H | Cl | H | H |
| L | $OCF_3$ | H | H | H |

The following examples are presented to illustrate certain embodiments of the present invention, and should not be construed as limiting the scope of this invention.

EXAMPLE 1

Benzhydryl-(4-chloro-2-iodo-phenyl)-amine

A solution of benzhydrol (13.5 g, 73.3 mmol) and acetonitrile (56 mL) was added over 1 h to a warm (80° C.), stirred solution of 2-chloro-4-iodoaniline (16 g, 63.1 mmol), benzenesulfonic acid (0.323 g, 2.0 mmol) and acetonitrile (53 mL). The solution was maintained at 80° C. for an additional 2.5 h. The mixture was allowed to cool to room temperature. Water (31 mL) was added over 1 h to the stirred mixture. The mixture was stirred for 2 h at room temperature. The solid product was collected by filtration. The solid product was combined with methanol (67 mL) and warmed to reflux for 30 m. The mixture was allowed to cool to room temperature. The purified product was collected by filtration, washed with methanol (2×10 mL) and vacuum dried to give 22.3 g of benzhydryl-(4-chloro-2-iodo-phenyl)-amine with 99% purity (as determined by HPLC). Mp 107-110.

EXAMPLE 2

4-Chloro-benzenesulfonic acid but-3-ynyl ester

A solution of 3-butyn-1-ol (365 g, 5.21 mol), triethylamine (526 g, 5.21 mol), and toluene (419 mL) was added to a cooled (0-5° C.) stirred solution of 4-chlorobenzenesulfonyl chloride (1.0 kg, 4.74 mol) and toluene (2.10 L). The reaction temperature was maintained below 20° C. during the addition. Precipitation of triethylamine hydrochloride salt occurred during the reaction. The reaction mixture was stirred at room temperature for 2-4 h. The triethylamine hydrochloride byproduct was separated by filtration and washed with toluene (2×350 mL). The combined filtrates were concentrated to remove toluene under reduced pressure above 45° C. to maintain the residue as a liquid. 2-Propanol (1.20 L) was added to the residue and the stirred solution was cooled to 20-25° C. Water (1.80 L) was added over 15 m. The slurry of product and solvent was cooled to 0-5° C. and stirred for 1 h. The white solid product was collected by filtration, washed with 33% aqueous 2-propanol (v/v), and vacuum dried to give 4-chloro-benzenesulfonic acid but-3-ynyl ester with 99% purity (as determined by HPLC.

EXAMPLE 3

(3,4-Dichloro-phenyl)-methanesulfonamide

A solution of (3,4-dichloro-phenyl)-methanesulfonyl chloride (500 g, 1.93 mol) and acetone (470 mL) was added over 2 h to cooled (0-5° C.), stirred concentrated ammonium hydroxide (28%, 900 mL, 227 g $NH_3$, 13.3 mol). The reaction mixture was maintained below 12° C. during the addition. The reaction mixture was allowed to warm to room temperature and was stirred for 1 h. Water (900 mL) was added to the reaction mixture and it was stirred for 1 h. The white solid was collected by filtration, washed with cold water (2×500 mL), and vacuum dried to give 375 g (81%) of (3,4-dichlorophenyl)-methanesulfonamide with 99% purity (as determined by HPLC).

EXAMPLE 4

Carbamic acid, [(3,4-dichlorophenylmethyl)-sulfonyl]-1,1-dimethylethyl ester

A solution of di-tert-butyl-dicarbonate (390 g, 1.79 mol) and toluene (740 mL) was added over 1.5 h to a stirred, warm (45° C.) mixture of (3,4-dichloro-phenyl)-methanesulfonamide (370 g, 1.54 mol), 4-dimethylaminopyridine (18.8 g, 0.154 mol), triethylamine (234 g, 2.32 mol), and toluene (3.0 L). The reaction mixture was stirred at 45° C. for 2 h. The reaction mixture was cooled to 0-5° C. Tetrahydrofuran (185 mL) was added to the reaction mixture A 10% aqueous solution of phosphoric acid was added to the reaction mixture over 1 h, maintaining an internal temperature of <5 C. The organic phase was collected and washed with 2.5% aqueous sodium bicarbonate (2.0 L). The combined water phases were washed with tetrahydrofuran (200 mL). The combined organic phases were concentrated under reduced pressure to a volume of 2.5 L. The mixture was cooled in an ice bath, and heptane (3.7 L) was charged over 15 m to complete product precipitation. The mixture was stirred at 0-5° C. for 1-2 h. The product was collected by filtration, washed with heptane (2×750 mL), and vacuum dried at <35° C. to give 463 g (88%) of carbamic acid, [(3,4-dichlorophenylmethyl)sulfonyl]-, 1,1-dimethylethyl ester with 98% purity (as determined by HPLC).

EXAMPLE 5

N-BOC-N-but-3-ynyl-(3,4-dichloro-phenyl)-methanesulfonamide

A mixture of carbamic acid, [(3,4-dichlorophenylmethyl)sulfonyl]-, 1,1-dimethylethyl ester (443 g, 1.13 mol), 4-chloro-benzenesulfonic acid but-3-ynyl ester (332.5 g, 1.36 mol), granular potassium carbonate (359 g, 2.60 mol), and N,N-dimethylformamide (1.38 L) was combined stirred, and warmed to 55° C. The mixture was stirred and maintained at 50-55° C. for 21 h. Additional charges of potassium carbonate (about 40 g) were added at 4 h intervals. The mixture was cooled to 30° C. The potassium carbonate was removed by filtration. The potassium carbonate cake was washed with DMF (2250 mL). Water (600 mL) was added to the stirred filtrates over 30 m. The mixture was stirred at room temperature for 1-2 h after complete water addition. The solid was collected by filtration and washed with 50% v/v aqueous methanol (2×350 mL). The product was vacuum dried at <50° C. to give 412 g (81%) of N-BOC-N-but-3-ynyl-(3,4-dichloro-phenyl)-methanesulfonamide with 99% purity (as determined by HPLC).

EXAMPLE 6

N-t-butoxycarbonyl-N-{4-[2-(benzhydryl-amino)-5-chloro-phenyl]-but-3-ynyl}-C-(3,4-dichlorophenyl)-methanesulfonamide A warm (45° C.) solution of N-BOC-N-but-3-ynyl-(3,4-dichloro-phenyl)-methanesulfonamide (347 g, 0.885 mol), dichlorobis(triphenylphosphine)palladium (II) (3.50 g, 4.99 mmol), and DMF (700 mL) was added slowly over 8 h to a warm (55° C.), stirred mixture of benzhydryl-(4-chloro-2-iodo-phenyl)-amine (350 g, 0.833 mol), dichlorobis(triphenylphosphine)palladium (II) (3.5 g, 4.99 mmol), copper (I) iodide (20.0 g, 0.105 mol), triethylamine, (259 g, 2.56 mol), and DMF (250 mL). The reaction mixture was stirred and maintained at 55° C. for 30 m after complete addition. The reaction mixture was distilled at reduced pressure using a heating bath temperature of 40-45° C. to remove triethylamine. The reaction mixture was filtered through a celite pad. The pad was washed with DMF (40 mL). 2-Propanol (280 mL) was added to the filtrate. The mixture was warmed to 55° C. Water (280 mL) was added slowly over 1 h to the stirred mixture. The stirred mixture was maintained at 55° C. for 30 m after complete water addition. The mixture was cooled to 10° C. The solid product was collected by filtration and washed with cold 1/1 (v/v) IPA/water (2×300 mL). The solid was vacuum dried at <50° C. to give N-t-butoxycarbonyl-N-{4-[2-(benzhydryl-amino)-5-chloro-phenyl]-but-3-ynyl}-C-(3,4-dichlorophenyl)-methanesulfonamide (534.5 g, 94%) with 98% purity (as determined by HPLC).

EXAMPLE 7

N-[2-(1-Benzhydryl-5-chloro-1H-indol-2-yl)-ethyl]-C-(3,4-dichloro-phenyl)-methanesulfonamide A solution of N-t-butoxycarbonyl-N-{4-[2-(benzhydryl-amino)-5-chloro-phenyl]-but-3-ynyl}-C-(3,4-dichlorophenyl)-methanesulfonamide (400 g, 0.585 mol) and N,N-dimethylacetamide (800 mL) was added slowly over 1 h to a hot (150° C.), stirred mixture of copper (I) iodide (12.2 g, 0.064 mol) and N,N-dimethylacetamide (740 mL). The reaction mixture was stirred and maintained at 150° C. for an additional 2 h. The reaction mixture was cooled to 40° C. The mixture was filtered through a celite pad and the pad was washed with IPA (2×100 mL). An additional charge of IPA (1400 mL) was added to the filtrate. The mixture was stirred and warmed to 60° C. Water (2.2 L) was added to the mixture over 30 m, maintaining an internal temperature of 55-60° C. The mixture was held at 60° C. for 30 m, then it was cooled to 5° C. The solid product was collected by filtration and the cake was washed with cold IPA/water (3/2 v/v, 2×200 mL). The solid was vacuum dried at <50° C. to give N-[2-(1-benzhydryl-5-chloro-1 H-indol-2-yl)-ethyl]-C-(3,4-dichloro-phenyl)-methanesulfonamide (338 g, 99%) with 98% purity (as determined by HPLC).

EXAMPLE 8

4-{3-[1-Benzhydryl-5-chloro-2-(2-{[(3,4-dichlorobenzyl)-sulfonyl]amino}ethyl)-1H-indol-3-yl]propyl}benzoic acid A solution of boron trifluoride etherate (50.7 g, 0.357 mol) and methylene chloride (83 mL) was added over 10 min to a stirred, cooled (−20° C.) mixture of N-[2-(1-benzhydryl-5-chloro-1H-indol-2-yl)-ethyl]-C-(3,4-dichloro-phenyl)-methanesulfonamide (275 g, 0.471 mol), triethylsilane (1.42 mol), 4-(3-oxo-propyl)-benzoic acid ethyl ester (213.6 g, 1.04 mol), and methylene chloride (2.6 L). An exotherm was observed and the reaction temperature increased to −13° C. The reaction mixture was cooled to and maintained at −20° C. Trifluoroacetic acid (53.7 g, 0.471 mol) was added to the reaction mixture 30 min after complete addition of boron trifluoride. The reaction mixture was stirred at −20° C. for 2 h. The reaction mixture was added to a stirred solution of sodium bicarbonate (127 g, 1.51 mol) and water (1.37 L). The mixture was filtered through a celite pad and the pad was washed with methylene chloride (50 mL). The layers were separated. The aqueous layer was washed with methylene chloride (200 mL). The combined organic layers were concentrated to 1.1 L at ambient pressure. Ethanol (1.38 L) was added to the mixture. The mixture was concentrated to 1.1 L at ambient pressure. The stirred mixture was cooled to 50° C. and tetrahydrofuran (275 mL) and 50% aqueous sodium hydroxide (188 g, 2.35 mol) was added. The mixture was warmed to reflux for 30 min. The mixture was cooled to 50° C. and toluene (1.38 L), water (225 mL), and acetic acid (141 g, 2.35 mol) was added. The mixture was stirred for 30 min. The mixture was filtered through a celite pad. The layers were separated and the aqueous layer was washed with a solution of tetrahydrofuran and toluene (1/1 v/v, 100 mL). The organic layer was washed consecutively with 3% aqueous sodium bicarbonate (100 ml), saturated sodium chloride (100 mL), and water (2×125 mL). The organic layer was concentrated to 1.1 L at ambient pressure. Toluene (550 mL) was added and the mixture was concentrated to 1.1 L at ambient pressure. The mixture was allowed to cool to room temperature and stirred overnight. Heptane (110 mL) was added to the stirred mixture after precipitation of solid product was observed. The solid product was collected by filtration and washed with cold toluene (2×275 mL). The product was vacuum dried at 66° C. to give 4-{3-[1-benzhydryl-5-chloro-2-(2-{[(3,4-dichlorobenzyl)sulfonyl]amino}ethyl)-1H-indol-3-yl]propyl}benzoic acid (227 g, 65%) with a purity of 99% (as determined by HPLC). The product can be recrystallized from ethanol in 91% recovery. MP 190° C.

EXAMPLE 9

4-(3-Oxo-propyl)-benzoic acid ethyl ester

Ethyl 4-iodobenzoate (200 g, 0.725 mol) and allyl alcohol (63 g, 1.087 mol) are added to a stirred suspension of Sodium bicarbonate (152 g, 1.812 mol), tetrabutyl-ammounium bromide (117 g, 0.362 mol) and Palladium (II) acetate (3.2 g, 0.014 mol) in DMF (600 mL). The reaction mixture is warmed to 75-80° C. for 3-3.5 hours and cooled to 40° C. -50° C. Toluene (1 L) is added to the reaction mixture with vigorous agitation and the mixture is stirred for 15 min at room temperature. The resulting mixture is filtered through a celite pad. The pad is washed with toluene (2×200 mL). The filtrate and wash are combined, washed with water (3×1 L), evaporated to constant weight at 30° C.-40° C. and 10 mmHg. The crude product 147.5 g (98.8%, 84% by HPLC) of 4-(3-Oxo-propyl)-benzoic acid ethyl ester as dark brown oil is obtained. $^1$H NMR (DMSO-d$_6$): δ1.38 (t, 3H), 2.81 (t, 2H), 3.03 (t, 2H), 4.39 (q, 2H), 7.27 (d, 2H), 7.98 (d, 2H), 9.81 (s, 1H).

EXAMPLE 10

Purification of 4-(3-Oxo-propyl)-benzoic acid ethyl ester

Crude 4-(3-Oxo-propyl)-benzoic acid ethyl ester (52% purity as determined by HPLC) was dissolved in toluene (80 mL) and combined with water (100 mL). The mixture was stirred. A solution of sodium metabisulfite (55.4 g) and water (130 mL) was added over 45 min to the stirred solution. The reaction mixture was warmed to 32° C. for 1 h. The layers were separated and the aqueous layer was washed with toluene (2×25 mL). The layers were separated. Water (600 mL) and ethyl acetate (150 mL) were added to the aqueous layer. The mixture was stirred and cooled to 2° C. A solution of potassium carbonate (165 g) and water (160 mL) was added over 1 h to the stirred reaction mixture, maintaining an internal temperature of 0-2° C. The reaction mixture was warmed to 20-23° C. in 1 h and then stirred for 2 h. The layers were separated and the aqueous layer was washed with ethyl acetate (2×20 mL). The combined organic layers were washed with water (2×50 mL). The ethyl acetate was removed under reduced pressure at <24° C. to give purified 4-(3-Oxo-propyl)-benzoic acid ethyl ester (20.6 g, 41% recovery). The purity was 96% (as determined by HPLC). Mp 109° C.

EXAMPLE 11

(2,6-Dimethylphenyl)-methanesulfonamide

A solution of (2,6-dimethylphenyl)-methanesulfonyl chloride (452 g, 2.07 mol) and acetone (2.0 L) was added over 90 m to cooled (0-5° C.), stirred, concentrated ammonium hydroxide (28%, 900 mL, 227 g NH$_3$, 13.3 mol). The reaction mixture was maintained <10° C. during the addition. The reaction mixture was allowed to warm to room temperature and was stirred for 1 h. Water (2.0 L) was added to the reaction mixture and it was stirred for 1 h at 0-5° C. The white solid was collected by filtration, washed with cold water (2×1 L), and vacuum dried to give 349 g (85%) of (2,6-dimethylphenyl)-methanesulfonamide with 99% purity (as determined by HPLC).

EXAMPLE 12

Carbamic acid, [(2,6-dimethylphenyl)methyl-sulfonyl]-1,1-dimethylethyl ester

A solution of di-tert-butyl-dicarbonate (490 g, 2.25 mol) and toluene (100 mL) was added over 3 h to a stirred, warm (40° C.) mixture of (2,6-dimethylphenyl)-methanesulfonamide (325 g, 1.63 mol), 4-dimethylaminopyridine (19.9 g, 0.163 mol), triethylamine (248 g, 2.46 mol), and toluene (2.60 L). The reaction mixture was stirred at 40° C. for 2 h. The reaction mixture was cooled to 0-5° C. Tetrahydrofuran (650 mL) was added to the reaction mixture. A 10% aqueous solution of phosphoric acid (2.6 L) was added to the reaction mixture over 1 h, maintaining an internal temperature of <5 C. The organic phase was collected and washed with water (650 mL). The organic phase was collected and washed with 5% aqueous sodium bicarbonate (650 mL). The combined organic phases were concentrated under reduced pressure to a volume of 1.7 L. The mixture was cooled in an ice bath, and heptane (3.25 L) was charged over 1 hour to complete product precipitation. The mixture was stirred at 0-5° C. for 1-2 h. The product was collected by filtration, washed with heptane (2×650 mL), and vacuum dried at <35° C. to give 427 g (87%) of carbamic acid, [(2,6-dimethylphenyl)methylsulfonyl]-, 1,1-dimethylethyl ester with 98% purity (as determined by HPLC).

EXAMPLE 13

N-BOC-N-but-3-ynyl-(2,6-Dimethylphenyl)-methanesulfonamide

A mixture of carbamic acid, [(2,6-dimethylphenyl)methylsulfonyl]-, 1,1-dimethylethyl ester (415 g, 1.38 mol), 4-chloro-benzenesulfonic acid but-3-ynyl ester (349 g, 1.43 mol), granular potassium carbonate (382 g, 2.77 mol), and N,N-dimethylformamide (1.29 L) was combined stirred, and warmed to 50-55° C. The mixture was stirred and maintained at 50-55° C. for 21 h. Additional charges of potassium carbonate (about 40 9) were added at 4 h intervals. The mixture was cooled to 30° C. The potassium carbonate was removed by filtration. The potassium carbonate cake was washed with DMF (2×230 mL). Water (560 mL) was added to the stirred filtrates over 30 m. The mixture was stirred at room temperature for 1-2 h after complete water addition. The solid was collected by filtration and washed with 50% v/v aqueous methanol (2×330 mL). The product was vacuum dried at <50° C. to give 436 g (90%) of N-BOC-N-but-3-ynyl-(2,6-dimethylphenyl)-methanesulfonamide with 99% purity (as determined by HPLC).

EXAMPLE 14

N-[2-(1-Benzhydryl-5-chloro-1H-indol-2-yl)-ethyl]-C-(2,6-dimethylphenyl)-methanesulfonamide A warm (40-45° C.) solution of N-Boc-N-but-3-ynyl-(2,6-dimethylphenyl)-methanesulfonamide (44.4 g, 0.106 mol), dichlorobis(triphenylphosphine)palladium (II) (0.50 g, 0.713 mmol), and DMF (125 mL) was added slowly over 7 h to a warm (55° C.), stirred mixture of benzhydryl-(4-chloro-2-iodo-phenyl)-amine (50 g, 0.119 mol), dichlorobis(triphenylphosphine)palladium (II) (0.50 g, 0.713 mmol), copper (I) iodide (3.0 g, 15.7 mmol), triethylamine, (42.2 g, 0.418 mol), and DMF (75 mL). Toluene (250 mL) and water (250 mL) were added to the reaction mixture. The aqueous phase was separated and washed with toluene (2×100 mL). The combined organic phases were filtered through a celite pad. The filtrate was washed with an 8.3% aqueous solution of N-acetylcysteine (2×150 mL), then again with water (150 mL). The organic phase was washed with 5% aqueous sodium bicarbonate (150 mL), then again with water (150 mL). The organic phase was concentrated to a heavy oil under reduced pressure. The oil was dissolved in N,N-dimethylacetamide (DMA, 175 mL). This DMA solution was added over 1 hour to a stirred mixture of copper iodide (2.26 g, 11.8 mmol) and DMA at 150° C. The reaction mixture was stirred at 150° C. for an additional 2.25 hours. The reaction mixture was cooled to room temperature and filtered through a celite pad with a DMA wash (2×25 mL). 2-Propanol (400 mL) was added to the warmed (45-40° C.), stirred filtrate. Then water (600 mL) was added to the stirred, warm (45-50° C.) mixture over 1 hour. The mixture was cooled to room temperature and stirred for a minimum of 12 hours. The solid was collected by filtration and washed with 2-propanol (2×50 mL). The solid was vacuum dried at 50° C. to give N-[2-(1-benzhydryl-5-chloro-1H-indol-2-yl)-ethyl]-C-(2,6-dimethylphenyl)-methanesulfonamide (60.6 g, 94%) with 98% purity (as determined by HPLC).

EXAMPLE 15

4-{3-[1-Benzhydryl-5-chloro-2-(2-{[(2,6-dimethyl-benzyl)-sulfonyl]amino}ethyl)-1H-indol-3-yl] propyl}benzoic acid A solution of boron trifluoride etherate (55 g, 0.387 mol) and methylene chloride (75 mL) was added over 10 min to a stirred, cooled (−20° C.) mixture of N-[2-(1-benzhydryl-5-chloro-1H-indol-2-yl)-ethyl]-C-(2,6-dimethylphenyl)-methanesulfonamide (300 g, 0.552 mol), triethylsilane (192 g, 1.66 mol), 4-(3-oxo-propyl)-benzoic acid ethyl ester (250 g, 1.21 mol), and methylene chloride (2.8 L). An exotherm was observed and the reaction temperature increased to −9° C. The reaction mixture was cooled to and maintained at −20° C. Trifluoroacetic acid (63 g, 0.553 mol) was added to the reaction mixture 30 min after complete addition of boron trifluoride. The reaction mixture was stirred at −20° C. for 2 h. The reaction mixture was added to a stirred solution of sodium bicarbonate (138 g, 1.64 mol) and water (1.50 L). The mixture was filtered through a celite pad and the pad was washed with methylene chloride (150 mL). The layers were separated. The aqueous layer was washed with methylene chloride (300 mL). The combined organic layers were concentrated to 1.2 L at ambient pressure. Ethanol (1.50 L) was added to the mixture. The mixture was concentrated to 1.2 L at ambient pressure. The stirred mixture was cooled to 50° C. and tetrahydrofuran (450 mL) and 50% aqueous sodium hydroxide (221 g, 2.76 mol) was added. The mixture was warmed to reflux for 30 min. The mixture was cooled to 50° C. and toluene (1.50 L), water (300 mL), and acetic acid (166 g, 2.76 mol) was added. The mixture was stirred for 30 min. The mixture was filtered through a celite pad. The layers were separated and the aqueous layer was washed with a solution of tetrahydrofuran and toluene (1/1 v/v, 100 mL). The organic layer was washed consecutively with 3% aqueous sodium bicarbonate (100 ml), saturated sodium chloride (100 mL), and water (2×125 mL). The organic layer was concentrated to 1.2 L at ambient pressure. Toluene (600 mL) was added and the mixture was concentrated to 1.2 L at ambient pressure. The mixture was allowed to cool to room temperature and stirred overnight. Heptane (100 mL) was added to the stirred mixture after precipitation of solid product was observed. The solid product was collected by filtration and washed with cold toluene (3×300 mL). The product was vacuum dried at 66° C. to give 4-{3-[1-benzhydryl-5-chloro-2-(2-{[(2,6-dimethyl-benzyl)sulfonyl]-amino}ethyl)-1H-indol-3-yl] propyl}benzoic acid (317 g, 81%) with a purity of 96% (as determined by HPLC). The product can be recrystallized from ethanol/water in 91% recovery. MP 193° C.

EXAMPLE 16

Ethyl 4-{3-[5-chloro-2-(2-{[(2,6-dimethylbenzyl)-sulfonyl]amino}ethyl)-1-(diphenylmethyl)-1H-indol-3-yl]propyl}benzoate To a stirred mixture of N-{2-[5-chloro-1-(diphenylmethyl)-1H-indol-2-yl]ethyl}-1-(2,6-dimethylphenyl)methanesulfonimide (35.00 g, 64.44 mmol) and ethyl 4-(3-oxopropyl)benzoate (29.24 g, 141.77 mmol) in dichloromethane (250 mL) cooled to −5° C. was added triethylsilane (31 mL, d=0.728, 194.08 mmol) with a rinse of dichloromethane (100 mL). Cooling was continued to −20° C. A solution of boron trifluoride etherate (5.50 mL. d=1.12, 43.40 mmol) in dichloromethane (40 mL) was added dropwise over 5 min. The temperature rose to −15° C. When the temperature had dropped to −20° C. once more, the remnants of the boron trifluoride etherate were rinsed into the reaction vessel with dichloromethane (30 mL). The temperature was maintained between −15° C. and −20° C. for 40 min. Trifluoroacetic acid (5.0 mL, d=1.48, 64.90 mmol) was added and the stirred mixture was kept at −15° C. and −20° C. for 3 hours with monitoring with HPLC [85.89% yield (at 220 nm and excluding excess ethyl 4-(3-oxopropyl)benzoate)]. The mixture was poured into a stirred aqueous solution of sodium bicarbonate (20 g in 220 mL water) and stirred for 5 hours, allowing the mixture to warm to room temperature. The mixture was refrigerated overnight. The mixture was filtered and the layers were allowed to separate in a separatory funnel (100 mL rinse to complete transfer). The light blue aqueous phase was separated and the organic phase was washed with water (3×100 mL) until the washings were pH 7 (pH paper). The volume was made up 650 mL with dichloromethane. A 200 mL portion at room temperature was removed and distilled to a volume of 160 mL. The stirred solution was then distilled while adding dropwise 2B ethanol (260 mL) at such a rate that the level of liquid in the distillation flask remained at the 160 mL mark. The final boiling point of the solution was 80-80.5° C. The solution was allowed to cool. It was seeded at 68° C., allowed to cool to 50° C. and placed in a water bath at 50° C. The slurry of crystals was allowed to cool slowly to 26° C., and then to 5-10° C. with an ice/water bath. Further cooling to −10° C. was achieved using a dry ice/acetone bath. The stirred slurry was kept at −20° C. for 15 min and then filtered. The filter cake was washed with cold (−20° C.) 2B ethanol (3×20 mL). The mother liquor and washings deposited more product on standing. The wet cake weighed 17.68 g. After drying overnight in a vacuum oven at 54° C. the crushed product (weighing 9.52 g) was dried once more overnight to provide 9.46 g (65%). HPLC purity (area %) of the material was 97.84%. NMR data was consistent with the product.

Variations of the present invention not illustrated herein will occur to those skilled in the art. The present invention is not limited to the embodiments illustrated and described herein, but encompasses all the subject matter within the scope of the appended claims.

What is claimed is:

1. A method for making a compound of formula 1:

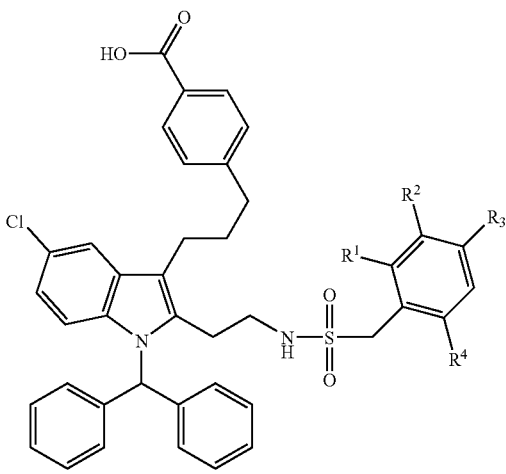

said method comprising the steps of:
a) reacting compounds of formulas 2 and 3:

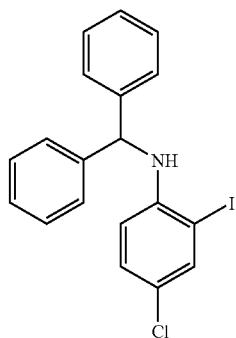

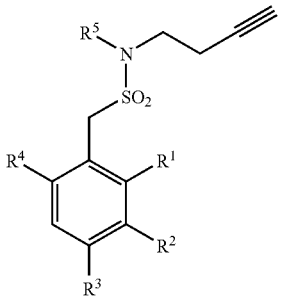

to produce a compound of formula 4:

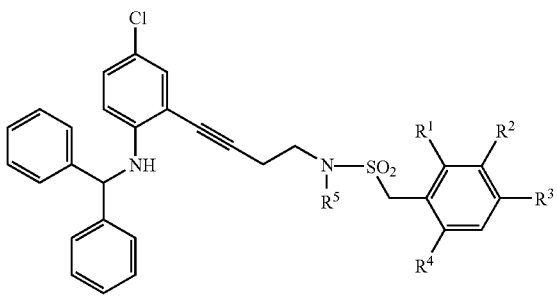

wherein:
$R^1$, $R^2$, $R^3$, and $R^4$ each is independently selected from the group consisting of H, halogen, —CN, —CHO, —$CF_3$, —$OCF_3$, —OH, —$NO_2$, —$C_{1-6}$ alkyl, —$C_{1-6}$ alkoxy, —$NH_2$, —NH($C_{1-6}$alkyl), —N($C_{1-6}$ alkyl)$_2$, and —NHC(O)—$C_{1-6}$ alkyl; and $R^5$ is selected from the group consisting of H and —C(O)O—$C_{1-6}$ alkyl, said reaction occurring in the presence of a base, a palladium catalyst, and a copper catalyst, wherein at least about 2 or more equivalents of the base are present; and b) converting the compound of formula 4 to the compound of formula 1.

2. The method of claim 1, wherein $R^1$, $R^2$, $R^3$, and $R^4$ each is independently selected from the group consisting of H, halogen, —$CF_3$, and —$C_{1-6}$ alkyl.

3. The method of claim 2, wherein $R^1$ is H, $R^2$ is Cl, $R^3$ is Cl, and $R^4$ is H.

4. The method of claim 2, wherein $R^1$ is —$CF_3$, $R^2$ is H, $R^3$ is H, and $R^4$ is H.

5. The method of claim 1, wherein about 2-4 equivalents of the base are present.

6. The method of claim 1, wherein about 0.5 mole % to about 1.5 mole % of the palladium catalyst is present.

7. The method of claim 1, wherein at least about 5 mole % or more of the copper catalyst is present.

8. The method of claim 7, wherein about 5 mole % to about 15 mole % of the copper catalyst is present.

9. The method of claim 1, wherein the base is selected from the group consisting of a trialkylamine, an alkali metal carbonate, an alkali metal bicarbonate, an alkaline earth metal carbonate, and an alkaline earth metal bicarbonate.

10. The method of claim 9, wherein the base is diisopropylethylamine, triethylamine, or a combination thereof.

11. The method of claim 1, wherein step b) comprises the step of reacting the compound of formula 4 with copper iodide to produce a compound of formula 5:

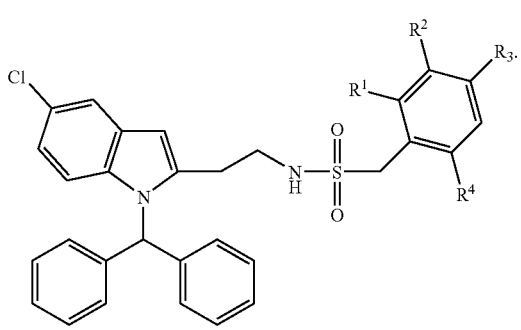

12. The method of claim 11, wherein step b) further comprises the step of reacting the compound of formula 5 with a compound of formula 6:

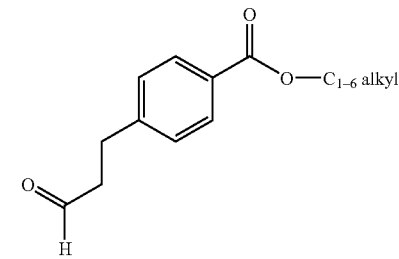

to produce a compound of formula 7:

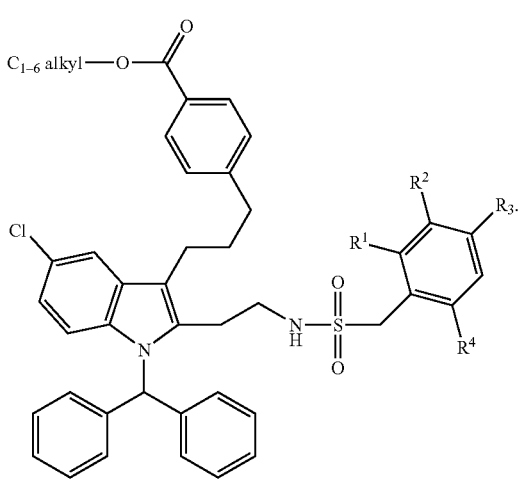

13. The method of claim 12, wherein the compound of formula 6 is purified by:
   a) treating the compound of formula 6 with aqueous metabisulfite solution to form a metabisulfite salt of the formula 6a:

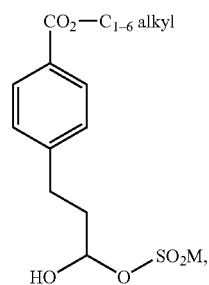

wherein M is Na or K, and
   b) treating the metabisulfite salt of formula 6a with a base to form the compound of formula 6.

14. The method of claim 12, wherein step b) further comprises the step of reacting the compound of formula 7 with a base to remove the ester $C_{1-6}$ alkyl group.

15. The method of claim 14, wherein the compound of formula 7 is not isolated prior to reacting with the base.

16. The method of claim 14, wherein the compound of formula 7 is isolated by crystallization prior to reacting with the base.

17. The method of claim 14, further comprising the step of recrystallizing the compound of formula 1 from a solvent comprising an alcohol.

18. The method of claim 17, wherein the alcohol is ethanol.

19. The method of claim 1, wherein the compound of formula 2 is prepared by reacting 2-iodo-4-chloroaniline with benzhydrol in the presence of an acid.

20. The method of claim 1 wherein the compound of formula 3 is prepared by reacting a compound of formula 8 with a compound of formula 9:

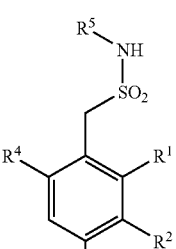

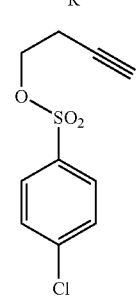

in the presence of a base, wherein $R^5$ is —C(O)O—$C_1$ alkyl.

21. The method of claim 1, wherein step b) further comprises:

(i) reacting the compound of formula 4 with copper iodide to produce a compound of formula 5:

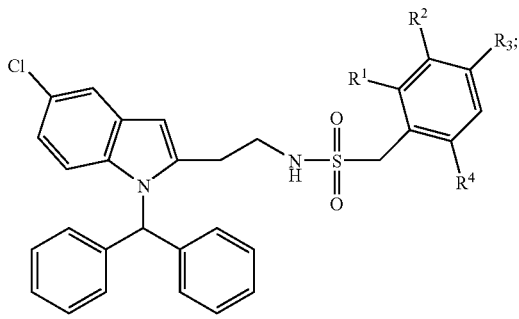

(ii) reacting the compound of formula 5 with a compound of formula 6:

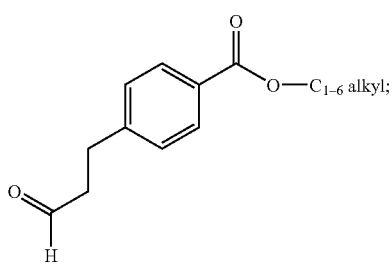

to produce a compound of formula 7:

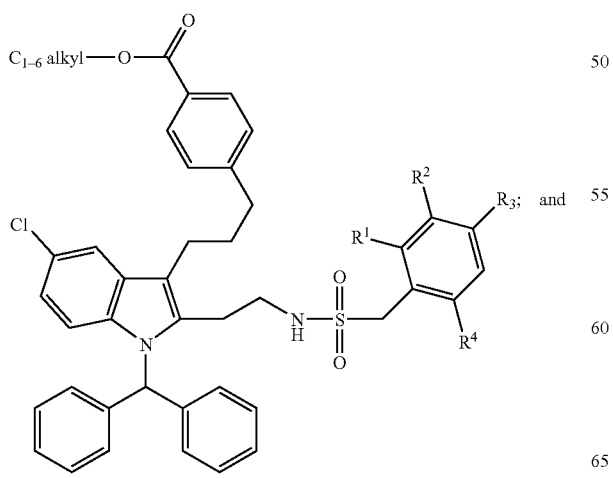

(iii) reacting the compound of formula 7 with a base to remove the ester $C_{1-6}$ alkyl group.

22. The method of claim 21, wherein $R^1$, $R^2$, $R^3$, and $R^4$ each is independently selected from the group consisting of H, halogen, —$CF_3$, and —$C_{1-6}$ alkyl.

23. The method of claim 22, wherein $R^1$ is H, $R^2$ is Cl, $R^3$ is Cl, and $R^4$ is H.

24. The method of claim 22, wherein $R^1$ is —$CF_3$, $R^2$ is H, $R^3$ is H, and $R^4$ is H.

25. The method of claim 21, wherein about 2-4 equivalents of the base are present.

26. The method of claim 21, wherein about 0.5 mole % to about 1.5 mole % of the palladium catalyst is present.

27. The method of claim 21, wherein at least about 5 mole % or more of the copper catalyst is present.

28. The method of claim 27, wherein about 5 mole % to about 15 mole % of the copper catalyst is present.

29. The method of claim 21, wherein the base is selected from the group consisting of a trialkylamine, an alkali metal carbonate, an alkali metal bicarbonate, an alkaline earth metal carbonate, and an alkaline earth metal bicarbonate.

30. The method of claim 29, wherein the base is diisopropylethylamine, triethylamine, or a combination thereof.

31. The method of claim 21, wherein the compound of formula 6 is purified by:

a) treating the compound of formula 6 with aqueous metabisulfite solution to form a metabisulfite salt of the formula 6a:

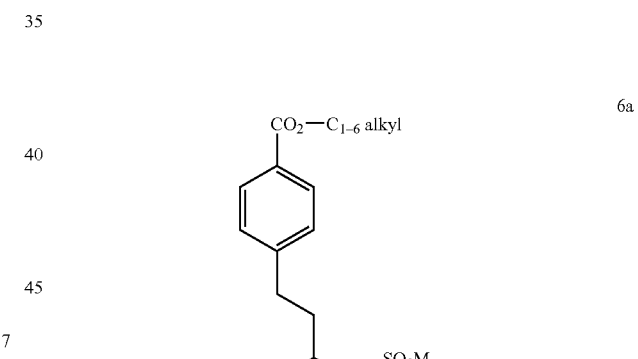

wherein M is Na or K, and b) treating the metabisulfite salt of formula 6a with a base to form the compound of formula 6.

32. The method of claim 21, wherein the compound of formula 7 is not isolated prior to reacting with the base.

33. The method of claim 21, wherein the compound of formula 7 is isolated by crystallization prior to reacting with the base.

34. The method of claim 21, further comprising the step of recrystallizing the compound of formula 1 from a solvent comprising an alcohol.

35. The method of claim 34, wherein the alcohol is ethanol.

36. The method of claim 21, wherein the compound of formula 2 is prepared by reacting 2-iodo-4-chloroaniline with benzhydrol in the presence of an acid.

37. The method of claim 21, wherein the compound of formula 3 is prepared by reacting a compound of formula 8 with a compound of formula 9:

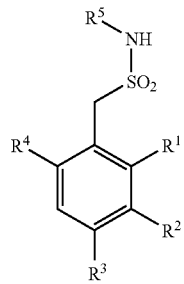
8

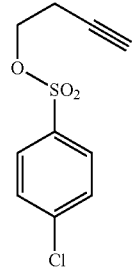
9 in the presence of a base, wherein $R^5$ is —C(O)O—$C_{1-6}$ alkyl.

* * * * *